US00PP32850P3

(12) United States Plant Patent
Francis

(10) Patent No.: US PP32,850 P3
(45) Date of Patent: Mar. 2, 2021

(54) APPLE TREE NAMED 'BELLA ROSA'

(50) Latin Name: *Malus domestica*
Varietal Denomination: Bella Rosa

(71) Applicant: Brendon Francis, Grove (AU)

(72) Inventor: Brendon Francis, Grove (AU)

(73) Assignee: Fruit Varieties International Pty Ltd, Grove (AU)

( * ) Notice: Subject to any disclaimer, the term of this patent is extended or adjusted under 35 U.S.C. 154(b) by 0 days.

(21) Appl. No.: 16/873,639

(22) Filed: May 27, 2020

(65) Prior Publication Data

US 2020/0383253 P1 Dec. 3, 2020

(51) Int. Cl.
*A01H 6/74* (2018.01)
*A01H 5/00* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Annette H Para
(74) *Attorney, Agent, or Firm* — Phase M Legal

(57) ABSTRACT

A new and distinct apple tree (*Malus domestica*) named 'Bella Rosa'. 'Bella Rosa' is a whole plant mutation of the variety 'Cripps Pink' and is distinguished by very early full pink-red color over the entire surface of the fruit, its spreading to drooping habit, and its solid flush color pattern.

7 Drawing Sheets

Latin name of the genus and species:
Botanical classification: *Malus domestica.*
Variety denomination: The new apple tree variety denomination is 'Bella Rosa'.

BACKGROUND OF THE VARIETY:

The present invention is a new and distinct cultivar of apple tree botanically known as *Malus domestica* and referred to by the cultivar name 'Bella Rosa'. 'Bella Rosa' was discovered as a naturally occurring whole plant mutation in a commercial orchard planting of the variety 'Cripps Pink' (U.S. Plant Pat. No. 7,880).

'Bella Rosa' was first observed in mid-March in Dover, Tasmania, Australia in 2013, where it was distinguished by its very early pink-red color over the entire fruit surface, even in shaded areas of the tree. 'Bella Rosa' is further distinguished from its parent by its solid flush pink-red color and high levels of fruit anthocyanin at 40 days after full bloom. 'Bella Rosa' is also distinguished from its 'Cripps Pink' parent by its drooping habit.

Asexual reproduction of the 'Bella Rosa' was carried out by bud grafting in 2014 and trees of the 'Bella Rosa' were planted for additional observation at Lucaston, Tasmania, Australia. 'Bella Rosa' has since been fruited through successive asexually propagated generations at Lucaston, Tasmania, Australia and has been observed to remain true to type with the distinguishing characteristics retained through successive generations of asexual reproduction.

BRIEF DESCRIPTION OF THE VARIETY

'Bella Rosa' is primarily distinguished from its parent 'Cripps Pink' by its very early full pink-red color over the entire surface of the fruit and its solid flush color pattern with its very high levels of fruit anthocyanin on young fruitlets at 40 days after full bloom. 'Bella Rosa' is further distinguished by its spreading to drooping habit in comparison to its parent 'Cripps Pink' and other similar commercial varieties. These and other distinguishing characteristics are set forth in the tables below.

Under similar growing conditions in Tasmania, Australia, under commercial practice, 'Bella Rosa' compares to its parent 'Cripps Pink' as described in Table 1 below:

TABLE 1

Comparison of 'Bella Rosa' to 'Cripps Pink'

| Characteristic | 'Cripps Pink' | 'Bella Rosa' |
|---|---|---|
| Tree vigor | Strong | Weak to medium |
| Tree habit | Upright | Drooping |
| One-year old shoot thickness | Thick | Medium |
| Fruit - area of overcolor | Small | Large |
| Fruit - intensity of overcolor | Light | Medium to Dark |
| Leaf - petiole length | Short | Medium |
| Leaf - petiole anthocyanin | Small | Large |
| Fruitlet overcolor | Absent | Large to very large |
| Fruit overcolor area | Small | Large |
| Fruit - Color pattern | Weak stripes with solid flush | Solid flush only |

A comparison of 'Bella Rosa' to 'PE' (U.S. Plant Pat. No. 30,144), the most similar variety of common knowledge, is set forth in Table 2 below:

TABLE 2

Comparison of 'Bella Rosa' to 'PE'

| Characteristic | 'PE' | 'Bella Rosa' |
|---|---|---|
| Fruit - area of overcolor | Very large | Large |
| Leaf petiole anthocyanin | Very Large | Large |
| Leaf blade incisions of margin upper half | Serrate type 1 | Serrate type 2 |
| One-year old shoot number of lenticels | 97 average per 100 mm of stem - Medium | 125 average per 100 mm of stem - Medium to many |

TABLE 2-continued

| Comparison of 'Bella Rosa' to 'PE' | | |
|---|---|---|
| Characteristic | 'PE' | 'Bella Rosa' |
| Tree Vigor | Strong | Medium |
| Tree Habit | Upright | Drooping |
| One-year old shoot thickness | Thick | Medium |
| Leaf petiole length | Short | Medium |

BRIEF DESCRIPTION OF THE PHOTOGRAPHS

Typical specimens of the tree, fruit and blossoms for the new apple tree variety 'Bella Rosa' are shown in the accompanying photographs for a three-year old tree planted on 'MM106' rootstock (unpatented). The colors shown are as true as possible within the usual limits of this kind of illustration.

DETAILED BOTANICAL DESCRIPTION OF THE VARIETY

Figure 1:
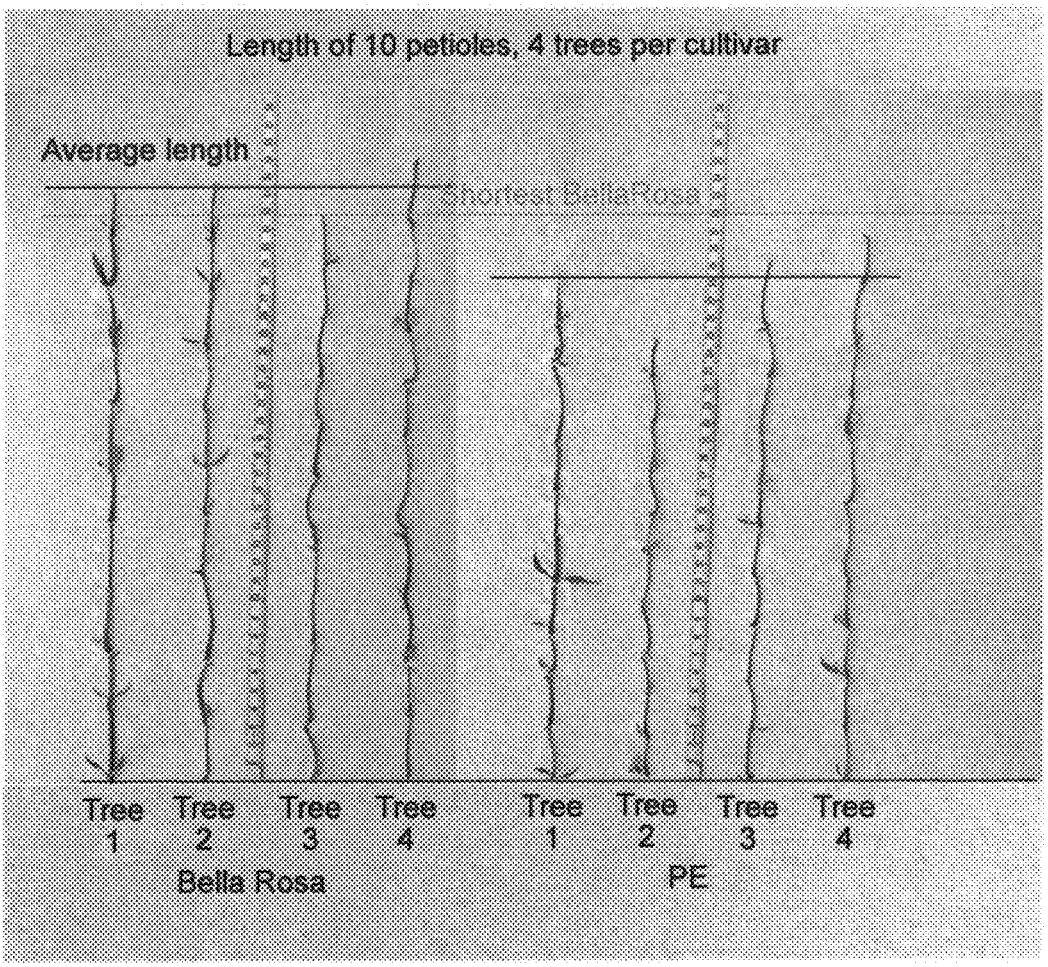
FIG. 1 shows petiole length of 'Bella Rosa' on the left compared to 'PE' on the right.
Figure 2:
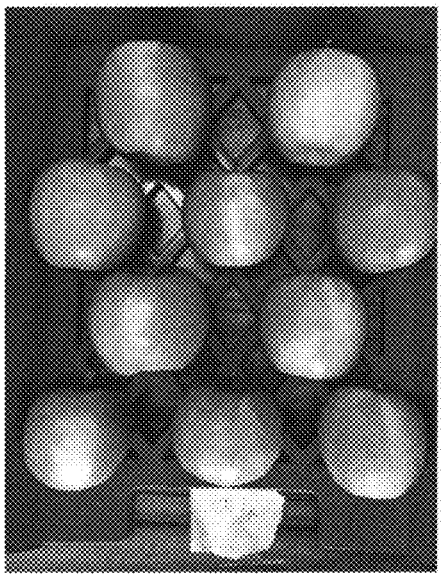
FIG. 2 shows current season's fresh fruit of 'Bella Rosa' (on the top) compared to fruit of 'Cripps Pink' (on the bottom), both harvested at maturity from trees of similar age and growing conditions.
Figure 2:
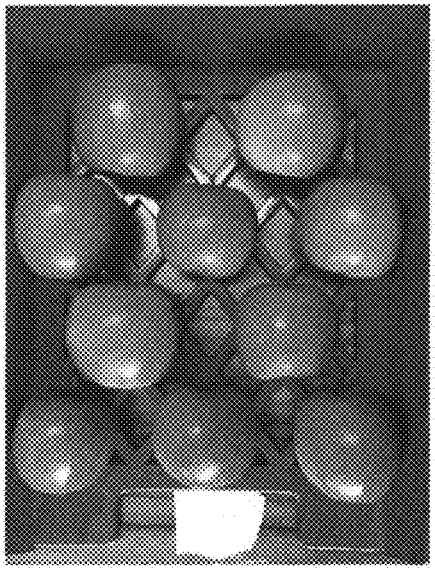
Figure 2:
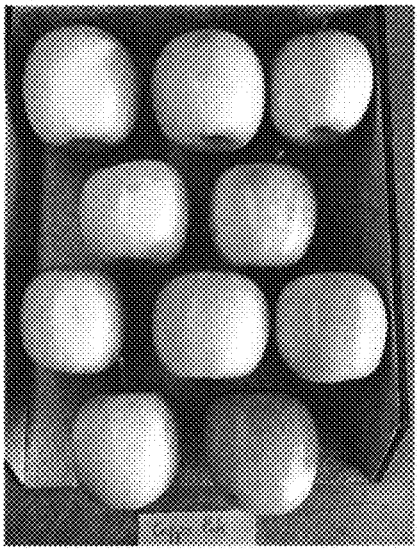
Figure 2:
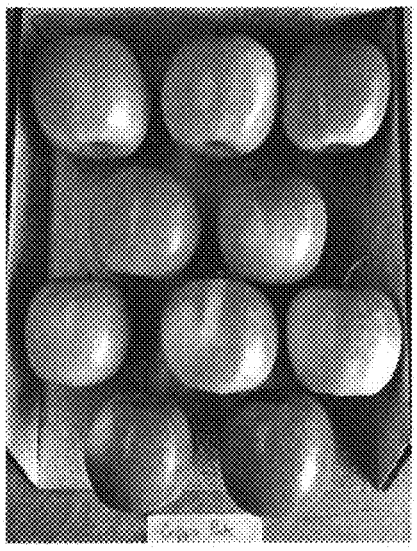
Figure 3:
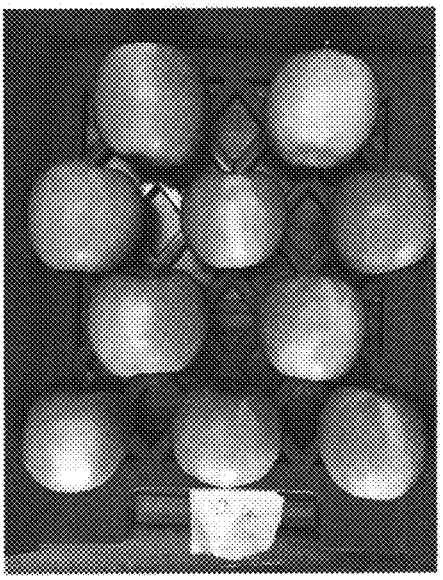
FIG. 3 shows current season's fresh fruit of 'Bella Rosa' (on the top) compared to fruit of 'PE' (on the bottom), both harvested at maturity from trees of similar age and growing conditions.
Figure 3:
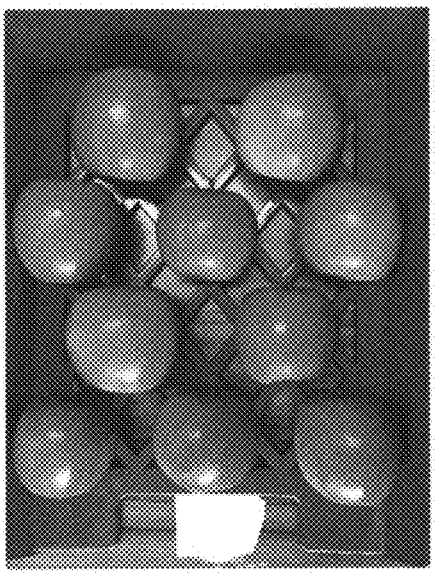
Figure 3:
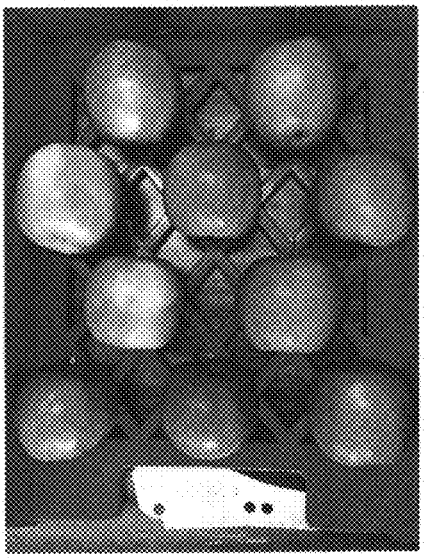
Figure 3:
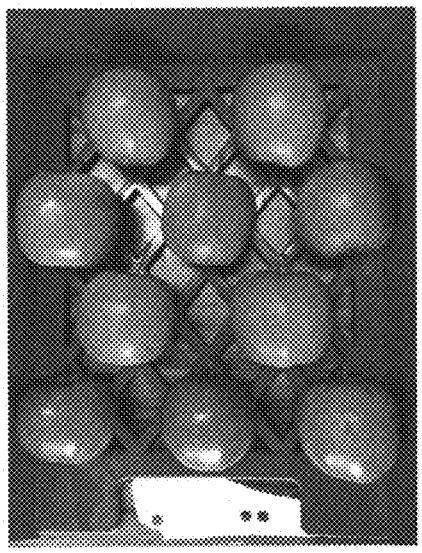
Figure 4:
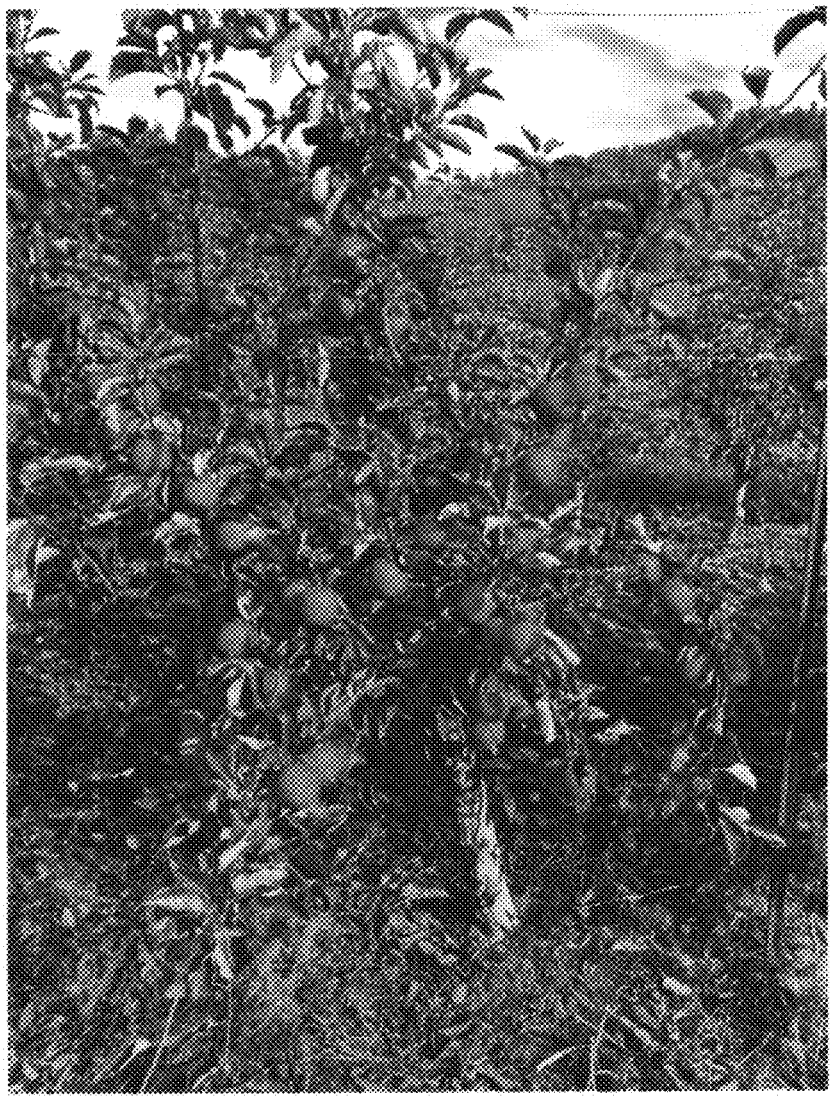
FIG. 4 shows a tree of 'Bella Rosa' in its third growing season on 'MM106' rootstock.
Figure 5:
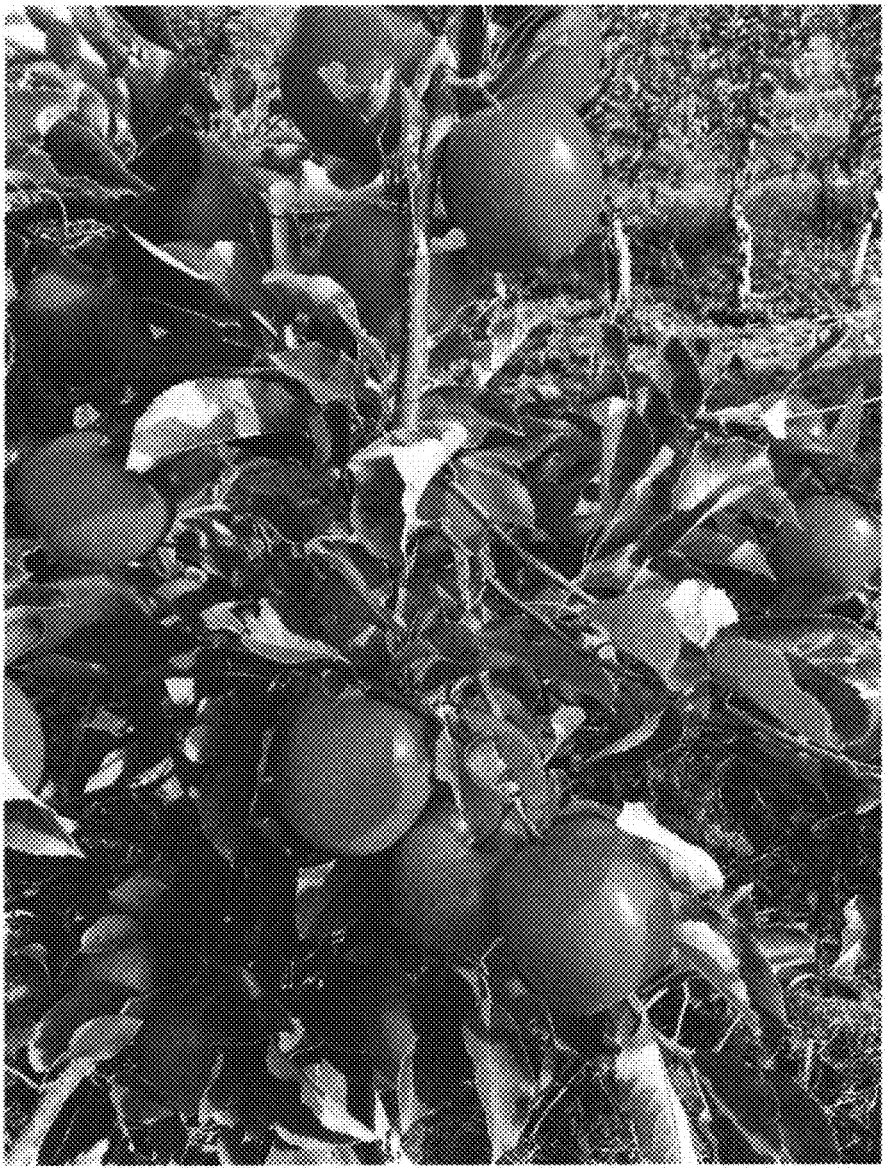
FIG. 5 shows the spreading and drooping nature of 'Bella Rosa' habit for a tree in its third growing season on 'MM106' rootstock.
Figure 6:
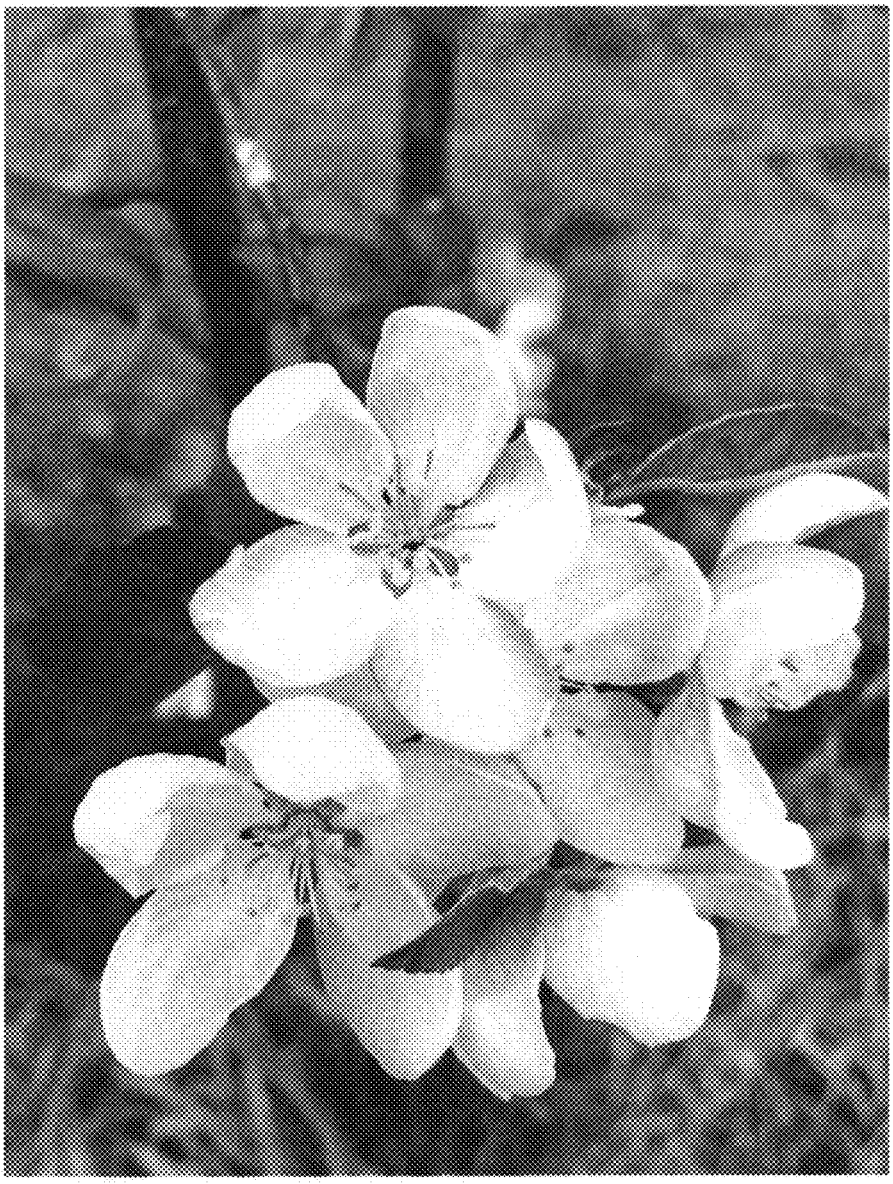
FIG. 6 shows a blossom of 'Bella Rosa' on a tree in its third growing season on 'MM106' rootstock; and, FIG. 7 shows a dormant tree of 'Bella Rosa' in its third growing season on 'MM106' rootstock with spreading and drooping branches.
Figure 7:
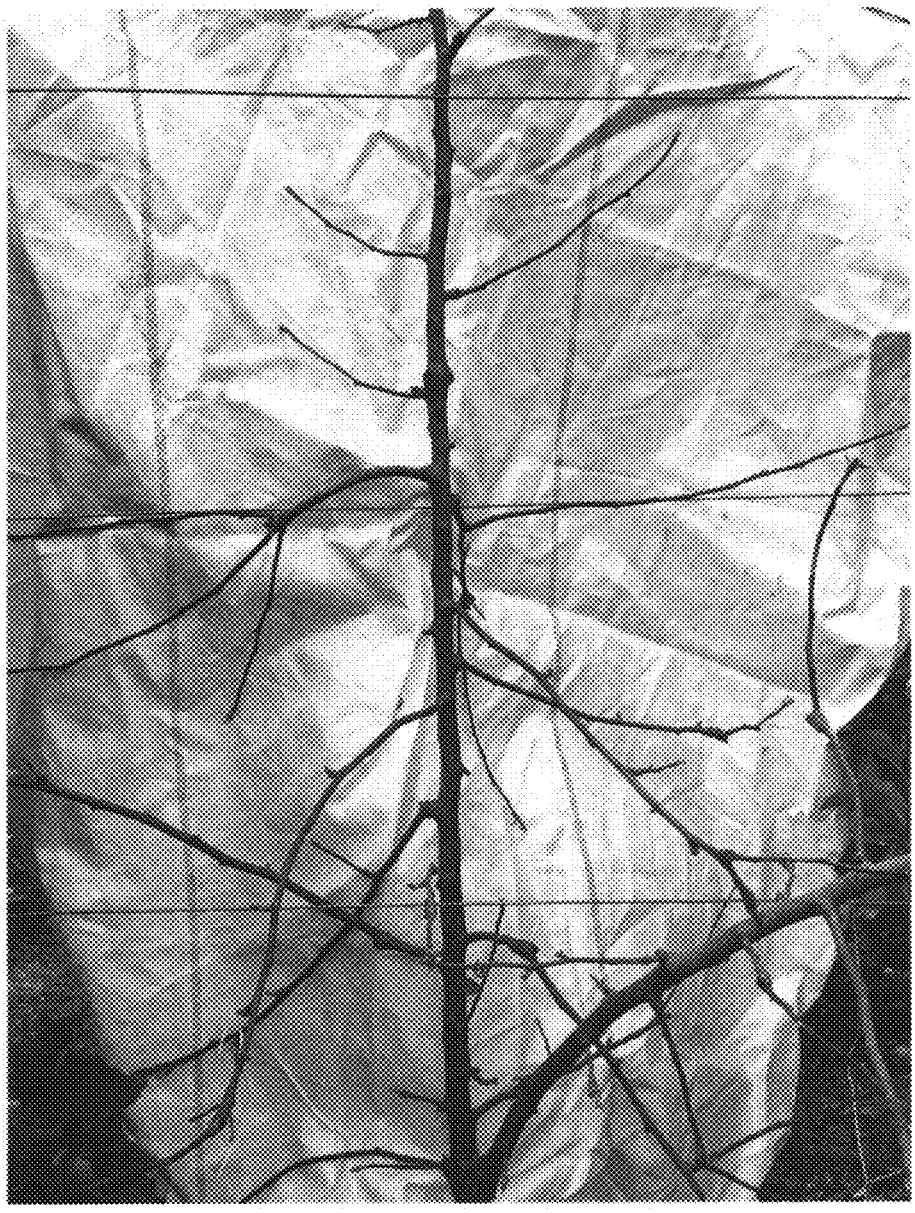

The following-detailed botanical description is based on observations made during the 2020 growing season at Lucaston, Tasmania, Australia of 4-year-old trees planted on 'MM106' rootstock (unpatented). The cultivar has not been observed under all possible environmental conditions. The phenotype may vary significantly with variations in the environment such as temperature, length of day and light intensity, without any variance in genotype. The characteristics described will vary somewhat depending upon cultural practices and climatic conditions and will vary with location and season. The plant and flower quantified measurements and foliage size are expressed as an average of measurements taken from several individual plants of 'Bella Rosa' using standard commercial cultural practices. The measurements of any individual plant or any group of plants of 'Bella Rosa' may vary from the stated average. All colors are described according to The Royal Horticultural Society Colour Chart ($5^{TH}$ edition 2007).

Tree:

*Vigor*.—Medium.

*Type*.—Ramified, cropping on spurs and long shoots.

*Habit*.—Drooping.

*Height*.—2.2 m.

*Trunk diameter*.—2.55 cm.

*Bark texture*.—Smooth with occasional ridging.

*Bark color*.—Yellow-green 148A on sun exposed side and on shaded side.

*Branch*.—Fruiting branches located at around 1.1 m above the graft union.

*Length*.—90 cm.

*Diameter*.—8.5 mm at base.

*Crotch angle*.—Drooping branches on unpruned tree. Branches on unpruned tree are horizontal to −8.5 degrees.

*Bark color*.—Greyed-red 178A on sun exposed side and Greyed-orange 165A on shaded side.

*Lenticel length*.—1.1 mm average.

*Lenticel color*.—Greyed-orange 164B.

*Quantity of lenticels per cm*$^2$.—5.

One-year old shoot:

*Length*.—45 cm average.

*Color*.—Greyed-red 178A on sun exposed side and Greyed-orange 165A on shaded side.

*Pubescence*.—Weak to medium on distal end of shoot.

*Thickness*.—4 mm average thickness mid shoot.

*Internode length*.—3.5 cm.

*Number of lenticels per cm*$^2$.—6 to 8 range — average of 125 per 100 mm.

Flower bud: 6.9 long mm on average.

*Color*.—Greyed-purple N187A.

*Shape*.—Elliptic.

Flowers:

*Diameter of fully open flower*.—48.5 mm.

*Relative position of petal margin*.—Free to touching.

*Quantity of flowers per cluster*.—5 to 7 range.

*Date of beginning of flowering*.—$8^{th}$ of October 2017 in Tasmania.

*Date of full bloom*.—$21^{st}$ of October 2017 in Tasmania.

*Pollination requirement*.—Pollination required by another diploid variety flowering at similar time.

Petals:

*Quantity per flower*.—5 petals per flower.

*Shape*.—Ovate to ellipsoid.

*Length*.—23.7 mm.

*Width*.—13.8 mm.

*Apex*.—Ovoid.

*Base*.—Cuneate to obovate at base.

*Margin*.—Smooth.

*Texture*.—Upper surface — Smooth.

*Texture*.—Lower surface — Smooth.

*Color*.—Upper surface — White in Color NN155C.

*Color*.—Lower surface — Red-Purple in Color 61B.

*Pistils*.—14.5 mm long; Yellow-Green Color 150C.

*Stigma*.—1.12 mm diameter; Yellow-Green Color 152A.

*Position of stigma relative to anther*.—Same level.

*Style*.—5 Fused and Pubescent at the base; Length 7.95 mm; Color: Yellow-Green 150C.

*Ovary*.—Pubescent; 2.53 mm diameter; Color Yellow-Green 150C.

*Anthers*.—16 to 18 per flower; Length 2.52 mm; Width 1.74 mm; Ample pollen, Color Yellow 6D.

*Pedicel*.—Length 35.31 mm; Diameter 1.84 mm; Color: Red-Purple 59A on sun exposed side; Color Yellow-Green 144B on shaded side.

*Sepals*.—Quantity 5; Length 8.95 mm; Width: 6.0 mm Color: Yellow-green 144B with Red-Purple 59A on tip; Recurved shape with smooth straight margin; Very Pubescent.

*Flower fragrance*.—Absent.

Leaves:

*Length*.—9.38 cm.

*Width*.—6.92 cm.

*Length/width ratio*.—1.36.

*Blade margin*.—Serrate Type 1.

*Shape*.—Oval to obtuse.

*Apex*.—Shape: Acute in shape.

*Base*.—Shape: Obtuse in shape.

*Pubescence*.—Description: Lightly pubescent on underside.

*Color*.—Upper surface — Green N137C.

*Color*.—Lower surface — Yellow-green 146B.

*Attitude in relation to shoot*.—Outward.

*Petiole*.—Length 37.9 mm; Diameter 1.87 mm; Color: Greyed-purple 185B.

*Mid rib*.—Greyed-purple 184C to Yellow-green 145D.

*Leaf vein*.—Extending from base of mid rib Greyed-purple 184C to two thirds of leaf mid vein to leaf tip Yellow-green 145D.

*Venation pattern*.—Arcuate from mid rib to Reticulate with smaller veins closer to leaf margins.

Fruit:

*Quantity per cluster*.—5 to 7 per cluster if no thinning occurs.

*Diameter*.—68 mm.

*Height*.—65 mm.

*Ratio of height to width*.—0.99.

*General shape in profile*.—Cylindrical.

*Position of maximum diameter*.—Near center.

*Ribbing*.—Moderate.

*Crowning at calyx end*.—Moderate.

*Size of eye*.—10.9 mm average width, Medium.

*Aperture of eye*.—Mostly closed, occasionally open.

*Length of sepal*.—5.8 mm average length, Medium.

*Bloom of skin*.—Absent or weak.

*Greasiness of skin*.—Absent or weak.

*Background color of skin*.—Yellow-green 150C.

*Amount of over color*.—Large, about 85%.

*Over color of skin*.—Red-purple 60A.

*Intensity of over color*.—Dark.

*Pattern of over color*.—Solid flush Only.

*Amount of russet around stalk cavity*.—Low to medium.

*Amount of russet on cheeks*.—Absent or small.

*Area of russet around eye basin*.—Absent or small.

*Length of stalk*.—33.1 mm on average, medium in length.

*Thickness of stalk*.—1.84 mm on average, thin to medium in width.

*Stalk color*.—Purple N79B.

*Depth of stalk cavity*.—14.2 mm on average.

*Width of stalk cavity*.—32.8 mm on average.

*Depth of eye basin*.—9.8 mm on average.

*Width of eye basin*.—31.4 mm on average.

*Flesh color*.—Yellow 11D.

*Flesh texture*.—Firm and crisp.

*Aroma*.—Fresh.

*Juiciness*.—Ample.

*Seeds*.—Minimum of 1, mostly 2 per cell; 9 per fruit; Acute; Greyed-orange 167B; Aperture of locules closed or slightly open.

Harvest:

*Harvest date*.—Time of Eating Maturity — Late season (Apr. 18, 2020 in Tasmania, Australia).

*Number of picks*.—One.

*Yield*.—65 kg from typical three-year-old tree.

*Disease/insect resistance/susceptibility*.—No resistance/susceptibility noted. Winter hardiness, cold tolerance, drought and heat tolerance are similar to parent variety. No unusual hardiness or tolerance noted.

Market use: Fresh. Observed fruit weight as an average of 10 typical fruit is 165 grams. Fruit is considered average to large for size.

*Percent soluble solids*, (*TSS*).—15.5% as an average of 10 typical fruit.

*Titratable acidity*.—0.6% as an average of 10 typical fruit.

*Penetrometer reading*.—9.1 kg as an average of 10 typical fruit.

I claim:

1. A new and distinct apple tree substantially as described and illustrated herein.

* * * * *

'Bella Rosa' Shaded Side at Harvest

'Bella Rosa' Sunny Side at Harvest

'Cripps Pink' Shaded Side at Harvest

'Cripps Pink' Sunny Side at Harvest

'Bella Rosa' Shaded Side at Harvest

'Bella Rosa' Sunny Side at Harvest

'PE' Shaded Side at Harvest

'PE' Sunny Side at Harvest